(12) United States Patent
Cotarca et al.

(10) Patent No.: US 8,969,597 B2
(45) Date of Patent: Mar. 3, 2015

(54) PROCESS FOR PREPARING NEBIVOLOL

(75) Inventors: Livius Cotarca, Cervignano del Friuli (IT); Johnny Foletto, Acrole (IT); Paolo Maragni, Virgilio (IT); Giorgio Soriato, Caldiero (IT); Daniele Urbani, Lendinara (IT); Massimo Verzini, Caldiero (IT)

(73) Assignee: Zach System S.p.A., Bresso (IT)

( * ) Notice: Subject to any disclaimer, the term of this patent is extended or adjusted under 35 U.S.C. 154(b) by 350 days.

(21) Appl. No.: 13/383,108

(22) PCT Filed: Jul. 23, 2010

(86) PCT No.: PCT/EP2010/004532
§ 371 (c)(1),
(2), (4) Date: Jan. 9, 2012

(87) PCT Pub. No.: WO2011/009628
PCT Pub. Date: Jan. 27, 2011

(65) Prior Publication Data
US 2012/0108826 A1 May 3, 2012

(30) Foreign Application Priority Data
Jul. 23, 2009 (IT) .............................. MI2009A1309

(51) Int. Cl.
*C07D 407/04* (2006.01)
*C07D 311/74* (2006.01)

(52) U.S. Cl.
CPC .................................. *C07D 407/04* (2013.01)
USPC .......................... 549/407; 549/356; 549/398

(58) Field of Classification Search
CPC ............................ C07D 311/74; C07D 407/04
USPC .......................................... 549/356, 398, 407
See application file for complete search history.

(56) References Cited

U.S. PATENT DOCUMENTS

| | | | | |
|---|---|---|---|---|
| 7,960,572 B2 * | 6/2011 | Volpicelli et al. | ............. | 549/398 |
| 7,999,124 B2 * | 8/2011 | Volpicelli et al. | ............. | 549/407 |
| 8,003,810 B2 * | 8/2011 | Ullucci et al. | ................ | 549/407 |
| 8,084,629 B2 * | 12/2011 | Volpicelli et al. | ............. | 549/407 |
| 8,258,323 B2 * | 9/2012 | Volpicelli et al. | ............. | 549/407 |

FOREIGN PATENT DOCUMENTS

EP          0 145 067 A2     6/1985

OTHER PUBLICATIONS

Fritz-Langhals, E.: "Separation of diastereomers by distillation—a new procedure for the synthesis of optically active heterocyclic carboxylic acids" Angewandte Chemie. Inernational Edition, Wiley VCH Verlag, Weinheim, vol. 32, No. 5, May 1, 1993,pp. 753-754, XP002008344 ISSN: 1433-7851.

* cited by examiner

*Primary Examiner* — Golam M M Shameem
(74) *Attorney, Agent, or Firm* — Silvia Salvadori, P.C.

(57) ABSTRACT

The present invention relates to a process for preparing Nebivolol and, more in particular, to a fractional distillation method of a mixture of stereoisomers of formula (I)

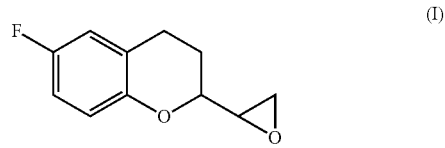

intermediates useful in the preparation of nebivolol.

10 Claims, No Drawings

PROCESS FOR PREPARING NEBIVOLOL

This application is a U.S. national stage of PCT/EP2010/004532 filed on Jul. 23, 2010 which claims priority to and the benefit of Italian Application No. MI2009A001309 filed on Jul. 23, 2009, the contents of which are incorporated herein by reference.

The present invention relates to a process for preparing Nebivolol and, more in particular, to a fractional distillation method of a mixture of stereoisomers of formula

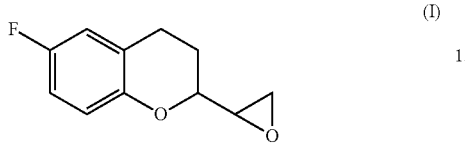

(I)

intermediates useful in the preparation of nebivolol.

Nebivolol (hereafter, NBV), is a mixture of equal amounts of [2S [2R* [R [R*]]]] α,α'-[imino-bis (methylene)] bis [6-fluoro-chroman-2-methanol] (hereafter d-NBV) of formula (IA)

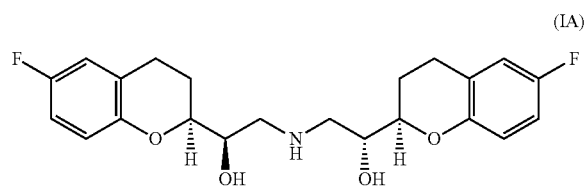 [SMILES: O[C@H](CNC[C@@H](O)[C@H]1CCc2cc(F)ccc2O1)[C@@H]1CCc2cc(F)ccc2O1]

(IA)

and its [2R [2S* [S [S*]]]] enantiomer (hereafter /-NBV) of formula (IB)

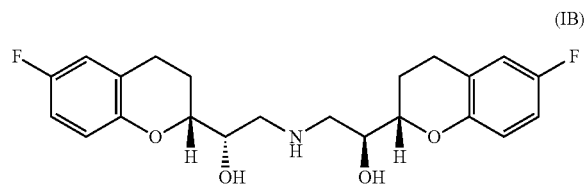 [SMILES: O[C@@H](CNC[C@H](O)[C@H]1CCc2cc(F)ccc2O1)[C@@H]1CCc2cc(F)ccc2O1]

(IB)

Nebivolol is characterized by its adrenergic β-blocking properties and is useful in treating essential hypertension. It has basic properties and may be converted into its addition salts through treatment with suitable acids. The hydrochloric acid addition salt is the marketed product.

It is known in the art that the synthesis of α,α'-[imino-bis (methylene)] bis [chroman-2-methanol] molecular structures is challenging for the skilled person because of the four asymmetric carbon atoms producing a mixture of 16 stereoisomers (in case of asymmetrical substitutions) or a mixture of 10 stereoisomers (in case of symmetrical substitutions). As apparent from the presence of symmetry in the nebivolol structure, a total of 10 stereoisomers may be generated.

Literature reports several processes for the preparation of nebivolol and/or of important synthesis intermediates.

Patent EP 0145067 (Janssen Pharmaceutica NV) describes a method of preparing NBV which comprises synthesizing diastereoisomeric mixtures of chroman epoxide derivatives in accordance with the synthetic scheme below

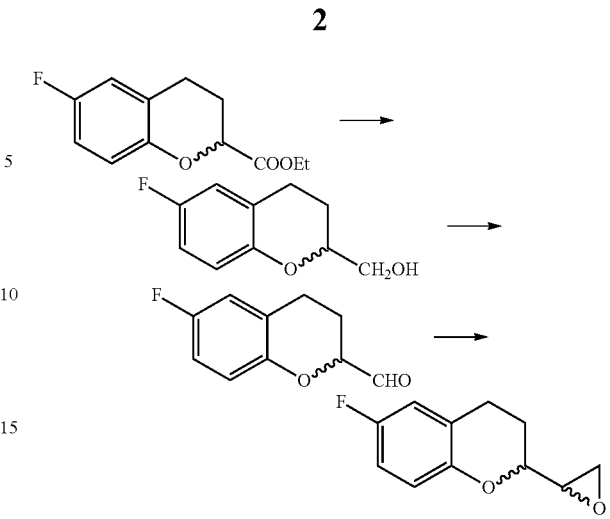

6-fluoro chroman carboxylic acid ethyl ester, derived from the esterification of the corresponding acid, is reduced with sodium di hydro bis-(2-methoxyethoxy)-aluminate to primary alcohol; the product is reacted with oxalyl chloride and then triethylamine at −60° C. to give corresponding racemic aldehyde, which is then converted into epoxide as a mixture of (R,S), (S,R), (R,R) and (S,S) stereoisomers. Example 17 describes the chromatographic separation of the epoxide intermediate into two racemic mixtures (R,S)-, (S,R)-epoxides (Mixture A) and (S,S)-, (R,R)-epoxides (Mixture B), respectively, which represent the key intermediates of the process for preparing NBV.

Patent EP 0334429 (Janssen Pharmaceutica NV) describes substantially the same synthetic process reported in the previous patent and is particularly directed to the preparation of single optical isomers (R,S,S,S) and (S,R,R,R) of NBV. In this instance, the 6-fluoro chroman carboxylic acid is resolved into single enantiomers by treatment with (+)-dehydroabiethylamine. Said single enantiomers are separately converted into their corresponding epoxides resulting in a mixture of two diastereoisomers. The following synthetic scheme describes, for example, the conversion of the S-acid derivative.

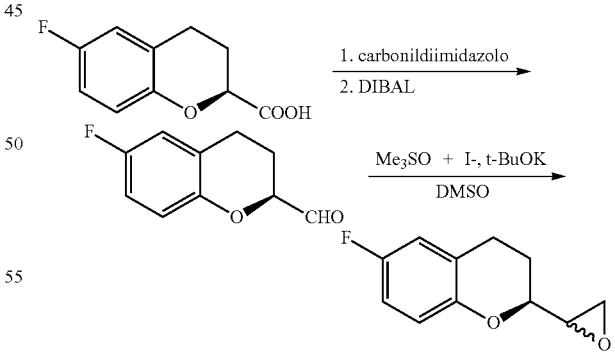

Examples 1 and 2 show the separation of said diastereoisomers into the single enantiomers through a chromatographic process, which when suitably combined give rise to the single optical isomers of NBV.

The subsequent international patent application WO 2006/025070 (Torrent Pharmaceuticals Ltd.), published around twenty years later than the above cited EP 0145067, describes an improved process for NBV synthesis wherein the epoxide mixture of formula I is separated into the known mixture A and mixture B through, again, column chromatography.

Moreover, patent EP 0744946 (Janssen Pharmaceutica NV) describes the separation of nebivolol hydrochloride from a mixture of (±)-[2R* [2S*,5S*(S*)]]+[2R*[1S*,5R*(R*)]] α,α'-[imino-bis(methylene)]bis[6-fluoro-3,4-dehydro-2H-1-benzopyran-2-methanol] through crystallization from ethanol. However, the yield in nebivolol hydrochloride is very low (6.6%).

To date, it seems that the development of the art has not been able to propose a valid alternative to the expensive chromatographic separation process. It is clear that the prior art is addressed towards alternative methods for preparing the epoxide derivatives or open analogues thereof substantially aimed at preventing said chromatographic separation of the mixtures useful for preparing the active ingredient. The trend seems to be that of developing asymmetrical syntheses or performing fractional crystallizations at various process levels capable of selecting the single isomers or the pure diastereoisomeric mixtures of interest.

The international patent application WO 2008/040528 in the name of the same Applicant describes an improved method for the synthesis of 6-fluoro chroman epoxides which comprises the conversion of an alkyl or aryl 6-fluoro-3,4-dehydro-2H-chromen-2-carboxylate into 2-halo-1-(6-fluoro-3,4-dehydro-2H-chromen-2-yl) ethanone via sulfoxonium ylide; the reduction of said alpha-haloketone to give corresponding 2-halo-1-(6-fluoro-3,4-dehydro-2H-chromen-2-il)-ethanol; and the cyclization in the presence of a base to give the corresponding epoxide derivative as a mixture of four (R,S), (S,R), (R,R) and (S,S) stereoisomers, respectively. The patent application further provides for the process to be applied to optically active substrates.

The international patent application WO 2008/010022 (Cimex Pharma AG and University of Zurich) describes an alternative process for the preparation of NBV in racemic form and of its pure enantiomers.

The process foresees, inter alias, to provide a compound of formula

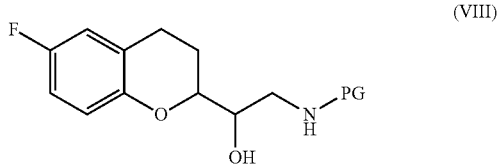

as a diastereoisomerically pure compound comprising at least 95% of RS/SR or RR/SS configuration wherein PG is hydrogen or an amine protecting group. Within said process, several methods are described for reducing a ketone precursor intermediate of the compound of formula VIII into two possible racemic mixtures having sin (RR/SS) or anti (RS/SR) configuration. It is clear that the aim is to cope with the problem of separation through a diastereoselective reduction of said ketone intermediates. However, the attempts performed had as a result the obtainment of racemic mixtures having variable ratios of the RR/SS over RS/SR configurations. Given the lack of success of the hypothesis of a diastereoselective reduction that leads to high diastereoisomeric excesses able to avoid a chromatographic separation, the patent application provides for a fractional crystallization of the mixture of the compounds of formula VIII which would allow obtaining mixtures of stereoisomers useful for the pros-ecution of the synthesis. Of note is the presence after crystallization of an amount of around 5% by weight of the undesired pair of stereoisomers.

The co/pending patent application PCT/EP2009/053051 in the name of the same Applicant describes an efficient method for the synthesis of 6-fluoro-chroman epoxides in the form of racemic mixtures useful in the preparation of NBV, via a diastereoselective reduction of known alpha-haloketones through the use of (+)- or (−)-B-chlorodiisopinocampheylborane as a reducing agent.

The international patent application WO 2006/016376 (Hetero Drugs) describes a process for separating a desired pair of diastereoisomers from a mixture of diastereoisomeric pairs through fractional crystallization. The process is applied to synthesis intermediates with a structure very similar to the end product, nebivolol.

The essential role of 6-fluoro-chroman epoxide intermediate in preparing NBV is known in the art. In light of the specific stereochemistry of the active ingredient, the role of said epoxide in the form of a useful racemic mixture or of the related single stereoisomers is even more critical. For separation purpose, the processes known in the art require expensive chromatographic processes that, as known, are absolutely undesired if intended for industrial manufacture.

Despite the efforts of the research aimed at finding alternative processes, it would be topical and desirable to study methods for preparing the epoxide intermediate, which allow overcoming the drawbacks presented by the processes described in the art, in particular, with the aim of by-passing the chromatographic step.

We have now, surprisingly, found a simple and efficient synthesis of 6-fluoro-chroman epoxides in the form of racemic mixtures useful in the preparation of NBV, via fractional distillation of the mixture containing the four possible stereoisomeric forms.

Therefore, it is a first object of the present invention a process for the separation of a compound of formula

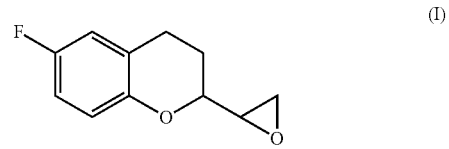 [SMILES: Fc1ccc2c(c1)CCC(C1CO1)O2]

to give a compound of formula

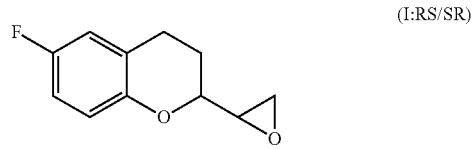 [SMILES: Fc1ccc2c(c1)CCC(C1CO1)O2]

as a diastereoisomerically pure compound of RS/SR configuration; and a compound of formula

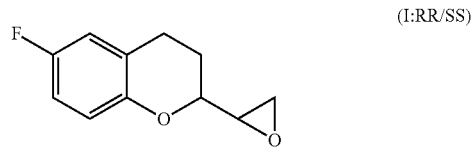 [SMILES: Fc1ccc2c(c1)CCC(C1CO1)O2]

as a diastereoisomerically pure compound of RR/SS configuration; characterized in that said separation is carried out by fractional distillation.

The compound of formula I can be prepared according to known techniques, in particular, according to the processes described in patent EP0145067 and in patent applications WO 2008/040528, EP1803715 and EP1803716.

The separation of the compound of formula 1 to give the diastereoisomerically pure compound of formula (I:RS/SR) and the diastereoisomerically pure compound of formula (I:RR/SS) is carried out by a fractionation process.

The fractional distillation method per se is well known to the man skilled in the art and, in general terms, it consists in the vaporisation of a liquid phase by heating and in the subsequent condensation by cooling in a site differing from that used for vaporisation; in the specific case of fractional distillation between said vaporisation site and that for condensation, a fractionating column is inserted to increase the efficiency of the separation process.

Such process is applicable to the two pure components of formula (I:RS/SR) and (I:RR/SS) since they exhibit a sufficiently high relative volatility (α) in the range of pressures/temperatures suitable for a practical industrial application.

Assuming an ideal behaviour of the mixture of the two components of formula (I:RS/SR) and (I:RR/SS) both in liquid phase and in vapour phase, the relative volatility (α) essentially depends on temperature and may be calculated by using equations known to the man skilled in the art.

The distillation process is carried out by using fractionating columns having dimensions (inside diameter and height) suitable for the amount of product to be distilled and for the type of packing material/operating efficiency (No. of theoretical plates) required to carry out the separation and obtain the two diastereoisomerically pure compounds of formula (I:RS/SR) and (I:RR/SS) with the desired quality (purity).

Preferably, the method object of the invention is carried out by using fractionating columns which use packing materials available on the market such as Sulzer, Koch, VICO known to the man skilled in the art.

The fractionation process object of the present invention is carried out by using a boiler temperature range comprised between 130° C. and 230° C. and applying a residual pressure on the column head of less than 2 mmHg.

Preferably, said fractionation process is carried out by using a boiler temperature range comprised between 160° C. and 200° C.

Preferably, said distillation is carried out by applying a residual pressure on the column head around 1.4-1.5 mmHg.

In a preferred aspect of the invention, such process is carried out by a batch distillation method under vacuum conditions suitable for keeping, at full speed, the operating temperature of the boiler to a value not exceeding 200° C. so as to ensure the stability of the compound of formula i within the time range required to complete the separation.

Preferably, the fractionation process is applied to a compound of formula I with purity (titre) of at least 92% w/w.

To this end, in a further preferred aspect of the invention, the mixture of the compounds of formula 1, obtained according to the methods described above, is pre-treated for example by subjecting it to a flash distillation operation (without fractionation) to give a compound of formula I with a purity (titre) of at least 95% w/w.

In the present invention, the expression "to give a compound of formula (I:RS/SR) as diastereoisomerically pure compound of RS/SR configuration" means a compound obtained as a substantially pure mixture of the optical isomers of RS and SR configuration, i.e, of the enantiomers (R)-6-fluoro-3,4-dihydro-2((S)-oxiran-2-yl)-2H-chromen and (S)-6-fluoro-3,4-dehydro((R)-oxiran-2-il)-2H-chromen.

In the present invention, the expression "to give a compound of formula (I:RR/SS) as diastereoisomerically pure compound of RR/SS configuration" means a compound obtained as a substantially pure mixture of the optical isomers of RR and SS configuration, i.e. of the enantiomers (R)-6-fluoro-3,4-dehydro((R)-oxiran-2-yl)-2H-chromen and (S)-6-fluoro-3,4-dehydro((S)-oxiran-2-il)-2H-chromen.

For the purposes of the present invention the relative amount of four stereoisomers in the mixture of compounds of formula I is not relevant.

Thus, it is evident to the skilled person that the process of the invention can be applied to partially resolved compounds of formula I wherein one or more stereoisomers are missing or, otherwise, present in a different percentage.

In one embodiment of the invention the fractional distillation is carried out on a partially resolved compound of formula

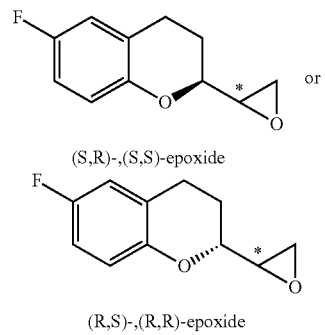

(S,R)-,(S,S)-epoxide (R,S)-,(R,R)-epoxide to give a diastereoisomerically pure compound of SR and SS or RS and RR configuration, respectively.

Said partially resolved compound in the form of diastereoisomeric mixture can be prepared in accordance with known methods such as those reported in the above cited EP334429 document.

Nevertheless, it is readily apparent that it is preferable to obtain a pure racemic mixture of the compounds of formula (I:RS/SR) and (I:RR/SS) defined above which, appropriately treated, lead to the preparation of the end product NBV. Said partially resolved epoxide derivatives and endowed with high purity represent, as known, key intermediates in the process for preparing NBV.

It is a further object of the present invention a process for the preparation of nebivolol which comprises the separation of a compound of formula

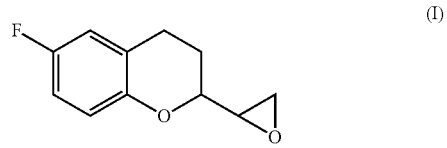 [SMILES: Fc1ccc2c(c1)CCC(C1CO1)O2]

(I)

to give a diastereoisomerically pure compound of formula (I:RS/SR) and (I:RR/SS) as described above.

The known mixtures of stereoisomers obtained through the separation process object of the present invention (Mixture A and Mixture B) are converted into the end product, Nebivolol, according to known techniques.

In a preferred aspect of the invention, Mixture A and Mixture B are processed according to what described in the international patent application WO 2008/064826 in the name of the same Applicant.

To the best of current inventors knowledge, the separation of the pairs of diastereoisomers useful for preparing NBV from the mixture of compounds of formula I by fractional distillation has never been disclosed nor suggested by the prior art.

It should be noted that in fine chemical processes, the man skilled in the art that needs to approach a separation of compounds provided with multiple chiral centres is certainly addressed towards classical methods such as column chromatography and/or fractional crystallisation.

As mentioned above, the prior art fully reflects this trend.

Therefore, we deem not obvious to industrially develop a fractional distillation applied to the specific pairs of diastereoisomeric derivatives object of the invention.

In particular, such application is even more unexpected in the presence of categories of substrates which, by their nature, are weak and/or reactive such as heterocyclic nuclea and, in particular, heterocyclic nuclea linked to tensioned oxirane rings.

In fact, it is known that a fractional distillation process necessarily implies a high thermal stress and, in addition, extended over time.

In any case, the most relevant inventive aspect that can be associated to the process of the invention is without any doubt the possibility to avoid the chromatographic separation of the intermediates with an optical configuration useful to the process for preparing the racemic mixture of NBV.

In fact, the drawbacks associable to the use of a chromatographic process at industrial level are known, mainly, in economic (costs resulting from apparatus, columns, stationary phases as well as from maintenance thereof) and environmental (use of very large amounts of solvents and consequent waste disposal) terms.

Moreover, the distillation process object of the invention is capable of providing a product characterised by high diastereoisomeric excesses (de of the compounds of formula (I:RS/SR) and (I:RR/SS) of at least 99%) and by low enantiomeric excesses.

Mixtures A and B are surprisingly obtained with a purity higher than that experimentally found by a chromatographic separation process applied on a comparable scale (titre of the compounds of formula (I:RS/SR) and (I:RR/SS) of at least 99% w/w).

Therefore, we not only believe that it is not suggested by the prior art to separate the specific pairs of diastereoisomers by the method object of the invention, but also obtaining a product provided with such high chemical and optical purity certainly unexpected.

The process of the present invention provides for the use of apparatus readily available on the market and is particularly suitable for the application on an industrial scale, It is important to note how once set up in its operating parameters a fractional distillation process can ensure higher reproducibility of the expected results (titre, diastereoisomeric purity) during the process scale up compared to a chromatographic process at an industrial level.

Moreover, it is important to note that in a fractional distillation process the control of the operating parameters can be ensured on industrial scale with simpler methods and thus at a lower cost than in a chromatographic process. A confirmation of this is the large diffusion of fractional distillation in the oil and petrochemical industry wherein the process is typically carried out in continuous.

Not obvious, on the contrary, the application described in the present invention, wherein a fractional distillation is used as separation technique to obtain diastereoisomerically pure intermediates of formula (I:RS/SR) and formula (I:RR/SS) useful for preparing a pharmaceutical active ingredient.

In addition, high yields and a nearly total recovery of the pairs of diastereoisomers (I:RS/SR) and (I:RR/SS) starting from the initial binary mixture subjected to the fractional distillation process, complete the picture. This recovery is obtained also using the simple recycle of the slop fraction (mixed fractions containing both pairs of diastereoisomers) obtained by the single batch distillation operation. Such slop fraction is reintroduced into the cycle in the boiler supply of the subsequent distillation operation.

Of course, it follows a considerable reduction of production costs and obtainment of a product with such purity as to be directly subjected to the subsequent nebivolol preparation process steps.

Hence, it is readily apparent how the separation method object of the invention constitutes an efficient and economical synthetic alternative in the preparation of key intermediates in the preparation of the active ingredient NBV.

A practical embodiment of the process object of the present invention comprises the optional flash distillation of a mixture of compounds of formula I to give said mixture with a purity higher than 92% w/w; the introduction into the boiler of the so obtained mixture; the heating of the boiler connected to a fractionating column at a temperature comprised between 130 and 230° C. and under reduced pressure conditions; the collection of useful fractions; and the optional recycle of the slop fractions in the subsequent distillation process.

To better illustrate the invention the following examples are now given.

EXAMPLE 1

Synthesis of compounds (R*)-6-fluoro-3,4-dihydro-2-((S*)-oxiran-2-yl)-2H-chromen (I: RS/SR) and (R*)-6-fluoro-3,4-dehydro-2-((R*)-oxiran-2-yl)-2H-chromen (I: RR/SS).

a) Distillation without Fractionation (Flash):

The compound of formula (I) 6-fluoro-3,4-dehydro-2-(oxiran-2-yl)-2H-chromen (1250.8 g) [diastereoisomeric ratio (I: RS/SR)(I: RR/SS)=1.13] was subjected to a preliminary operation of vaporisation/condensation under high vacuum conditions (115-138° C.; 1.7 mmHg). At the end of the operation most of the product charged (1241.2 g; assay GC: 96.1% w/w) is recovered.

b) Separation of the Diastereoisomers by Fractional Distillation:

The compound of formula (I) 6-fluoro-3,4-dehydro-2-(oxiran-2-yl)-2H-chromen resulting from the previous step (1232.0 g) was charged into a boiler consisting of a three-neck Pyrex glass flask, heated with an electrical skirt controlled by a power switch and fitted with glass capillary tube fed with nitrogen. The boiler is connected to a fractionating column consisting of two jacketed glass column sections with a 2 inch internal diameter (with adiabatic jacket) and a total height of about 1.2 meter filled with a packing material that ensures an efficiency corresponding to 10-25 theoretical plates. The column head is of the type with liquid distribution with water cooled dual jacket condenser (about 13° C.). The experimental apparatus is completed by two thermocouples for temperature detection at ° C. (one in the boiler and one at the head), an oil vacuum pump and a pressure measurement system.

During a single purification operation by batch fractional distillation a series of fractions was collected in the following order:
1. Head fractions containing light products: 13.7 g total;
2. Fractions containing the diastereoisomerically pure compound of formula (I: RS/SR): 479.8 g total; assay (HPLC) >99% w/w, diastereoisomeric excess>99.5%; Head Temp.=117° C., Boiler Temp.=161-162° C., vacuum=1.4-1.5 mmHg;
3. Mixed and slop fractions containing the compounds of formula (I: RS/SR) and formula (I: RR/SS) still in admixture: 242.4 g total; slop fract.: Head Temp.=123-126° C., Boiler Temp. =164-165° C., vacuum =1.5 mmHg;
4. Fractions containing the diastereoisomerically pure compound of formula (I: RR/SS): 275.1 g total; assay (HPLC) >99% w/w, diastereoisomeric excess>99%; Head Temp.=126° C., Boiler Temp.=165-199° C., vacuum=1.4-1.5 mmHg;
5. Fraction consisting of distillation end boiler+column dynamic hold up: 130.0 g total; containing the compound of formula (I: RR/SS) in diastereoisomeric excess>99%;
6. Fraction consisting of static column hold up: 86.9 g; containing a compound of formula (I: RR/SS) in diastereoisomeric excess=about 98%. Such fraction was recovered after concentration of the organic solution obtained by washing the distillation column with MTBE.

Diastereoisomer (I: RS/SR): $\delta_H$(400 MHz; CDCl$_3$) 6.84-6.73 (3H, m), 3.87-3.81 (1H, m), 3.15-3.10 (1H, m), 2.91-2.78 (4H, m), 2.18-2.10 (1H, m), 1.96-1,84 (1H, m).

Diastereoisomer (I: RR/SS): $\delta_H$(400 MHz; CDCl$_3$) 6.81-6.72 (3H, m), 3.88-3.82 (1H, m), 3.21-3.17 (1 H, m), 2.89-2.76 (4H, m), 2.1-2.00 (1H, m), 1.97-1.87 (1H, m).

The invention claimed is:
1. A process for obtaining a compound of formula

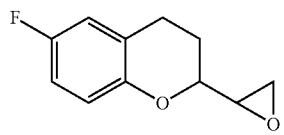

(I:RS/SR)

as a diastereoisomerically pure compound of RS/SR configuration, and a compound of formula

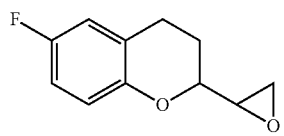

(I:RR/SS)

as a diastereoisomerically sure com ound of RR/SS configuration, said method comprising:
separating a compound of formula

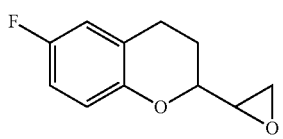

(I)

by fractional distillation; and
obtaining said compound of formula

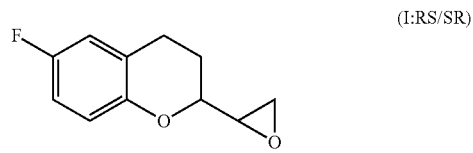 [SMILES: Fc1ccc2c(c1)CCC(C1CO1)O2]

(I:RS/SR)

as a diastereoisomerically pure compound of RS/SR configuration; and said compound of formula

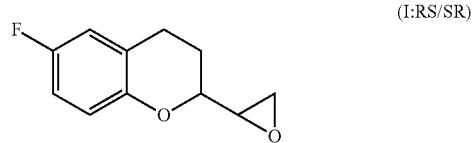 [SMILES: Fc1ccc2c(c1)CCC(C1CO1)O2]

(I:RS/SR)

as a diastereoisomerically pure compound of RR/SS configuration.

2. A process according to claim 1 wherein said distillation is carried out by using a boiler temperature range comprised between 130° C. and 230° C.

3. A process according to claim 2 wherein said distillation is carried out by using a boiler temperature range comprised between 160° C. and 200° C.

4. A process according to claim 1 wherein said distillation is carried out by applying a residual pressure on the column head of less than 2 mmHg.

5. A process according to claim 4 wherein said distillation is carried out by applying a residual pressure on the column head of around 1.4-1.5 mmHg.

6. A process according to claim 1 wherein said distillation is carried out by a batch distillation method.

7. A process according to claim 1 wherein said compound of formula I has an initial purity of at least 92%.

8. A process according to claim 1 further comprising a pre-treatment of the compound of formula I mixture by flash distillation.

9. The process according to claim 1 further comprising converting said I:RS/SR compound and said I:RR/SS compound into nebivolol.

10. A process according to claim 1 wherein said fractional distillation is carried out on a partially resolved compound of formula
in

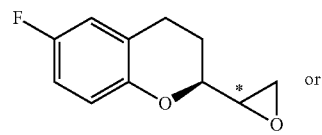

(S,R)-,(S,S)-epoxide

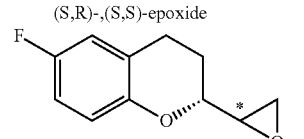

(R,S)-,(R,R)-epoxide the form of diastereoisomeric mixture.

* * * * *